(12) United States Patent
Möllstam

(10) Patent No.: US 9,901,670 B2
(45) Date of Patent: Feb. 27, 2018

(54) DEVICE FOR IRRIGATION AND INSUFFLATION WITH BLOOD PRESSURE DEPENDENT PRESSURE CONTROL

(71) Applicant: BonVisi AB, Nacka (SE)

(72) Inventor: Anders Möllstam, Nacka Strand (SE)

(73) Assignee: BONVISI AB, Nacka (SE)

( * ) Notice: Subject to any disclaimer, the term of this patent is extended or adjusted under 35 U.S.C. 154(b) by 264 days.

(21) Appl. No.: 14/737,571

(22) Filed: Jun. 12, 2015

(65) Prior Publication Data

US 2015/0290387 A1    Oct. 15, 2015

Related U.S. Application Data

(63) Continuation of application No. PCT/SE2014/051332, filed on Nov. 10, 2014.

(30) Foreign Application Priority Data

Nov. 8, 2013 (SE) ......................................... 1351319

(51) Int. Cl.
*A61M 3/02* (2006.01)
*A61B 1/015* (2006.01)
(Continued)

(52) U.S. Cl.
CPC ........... *A61M 3/0229* (2013.01); *A61B 1/015* (2013.01); *A61B 1/12* (2013.01); *A61B 5/021* (2013.01);
(Continued)

(58) Field of Classification Search
CPC .............. A61M 3/0229; A61M 13/003; A61M 3/0216; A61M 1/0058; A61M 5/021; A61M 1/015; A61M 2230/30; A61M 2205/3344
See application file for complete search history.

(56) References Cited

U.S. PATENT DOCUMENTS 6,024,720 A     2/2000 Chandler
8,540,667 B2 *  9/2013 Gerrans ........... A61B 17/32072
                                                604/96.01
(Continued)

FOREIGN PATENT DOCUMENTS

WO        92/22871 A1    12/1992
WO         9802205 A1     1/1998

*Primary Examiner* — Bradley Osinski
(74) *Attorney, Agent, or Firm* — Gabriela B. Tomescu, Esq.; Bergenstråhle & Partners AB

(57) ABSTRACT

A device for irrigation and/or insufflation during endoscopic surgery/procedures in a body cavity, comprising a first fluid pump device to deliver fluid to the body cavity, a second fluid pump device to move fluid from the body cavity, a control unit connected to the first and/or second fluid pump device, a blood pressure measuring device, wherein the control unit derives a control signal based on a signal from the blood pressure measuring device, and sends the control signal to the first fluid and/or second fluid pump device, wherein the control signal is derived by processing the signal from the blood pressure measuring device using a correlation factor in the device, dependent on the relationship between a blood pressure measurement signal, and a perfusion pressure of the body cavity, wherein the first and/or second fluid pump device controls the pressure in the body cavity based on the control unit's control signal.

24 Claims, 2 Drawing Sheets

(51) Int. Cl.
  *A61B 5/021*   (2006.01)
  *A61M 1/00*    (2006.01)
  *A61M 13/00*   (2006.01)
  *A61B 1/12*    (2006.01)
  *A61M 3/00*    (2006.01)

(52) U.S. Cl.
  CPC .......... *A61M 1/0058* (2013.01); *A61M 3/005* (2013.01); *A61M 3/0216* (2014.02); *A61M 3/0283* (2013.01); *A61M 13/003* (2013.01); *A61M 13/006* (2014.02); *A61B 2505/05* (2013.01); *A61M 2205/12* (2013.01); *A61M 2205/3303* (2013.01); *A61M 2205/3344* (2013.01); *A61M 2230/30* (2013.01)

(56) References Cited

U.S. PATENT DOCUMENTS

| | | |
|---|---|---|
| 2007/0249993 A1 | 10/2007 | Mollstam et al. |
| 2008/0154185 A1 | 6/2008 | Blight |
| 2008/0243054 A1 | 10/2008 | Mollstam et al. |

\* cited by examiner

DEVICE FOR IRRIGATION AND INSUFFLATION WITH BLOOD PRESSURE DEPENDENT PRESSURE CONTROL

This application is a continuation of PCT Application No. PCT/SE2014/051332, filed Nov. 10, 2014, which claims priority to Swedish Application No. SE 1351319-7, filed Nov. 8, 2013, the entire contents of each of which are hereby incorporated by reference.

TECHNICAL FIELD

This invention pertains to the medical field of endoscopic surgery, and in particular to the management of liquid and gas that is irrigated and insufflated into the surgical site during endoscopic procedures

BACKGROUND ART

Endoscopic surgery is performed within the natural cavities of the human body. A small hole is created in the skin of the patient and an optical instrument, the endoscope, is positioned in the cavity. The endoscope can consist of a rigid flexible tube having channels for light, fluid, gas etc depending on the endoscopy application. Specific applications of this procedure include: Transurethral resection (TUR), Laparascopy, enteroscopy, colonoscopy, sigmoidoscopy, proctoscopy, cytoscopy, arthoscopy, etc.

In the urology application, or transurethral resection (TUR), this technique is used in surgery of body cavities like prostate, bladder, urethra or kindly etc. Further in this patent application, the surgical site for an endoscopic procedure in general, will be referred to as the body cavity.

During endoscopic procedures the body cavity is not opened, instead the surgical area is made visible through a lens-device, an endoscope. To obtain a visible operation site the body cavity is pressurised with irrigation liquid or with gas. In the endoscopic procedures where liquid is used, normally TUR-, arthroscopy- and hysteroscopy procedures, the irrigation flushes the operation site and is some cases also put an over pressure in the site to extend it. Irrigation in these cases is performed through gravity or by means of a pump device. In the endoscopic procedures where gas is used it is always insufflated through a pump system.

The above-mentioned pump devices are further in this patent application referred to as an insufflator, an irrigation pump or just the pump.

The pump is used to irrigate or flush the body cavity with fluids or gas. The insufflator pump uses Carbone dioxide (CO2) as a rule, and the pump is usually an insufflation type pump, moving the gas from a gas container to the body cavity via a tube. The irrigation pump transports the fluids from a bag or container via a tube into the body cavity. Normally uses a sterile solution like saline or glycine and the pump is usually a peristaltic roller type pump. The pressure is set manually by practise in both pump types. It may be higher for certain body cavities, but setting of the pressure can also be done arbitrarily.

Existing liquid and gas management systems are either operated by a fixed flushing volume (i.e. Volumetric devices) programmed by the operator of the system when starting the procedure (normally an ml/min value), or by a fixed pressure target for the system. The operator of the system upon start of the process selects the target pressure. Existing pressure controlled systems have different ways of measuring the pressure, but the overall technique is indirectly measurement of the pressure on the irrigation side of the system, i.e. the delivery side.

A gas management system is most often used during Laparoscopy but have some safety limitation in this area. During the procedure 100% Carbone dioxide is pumped into the body cavity, i.e. intra-peritoneal. Carbone dioxide is potentially dangerous in relatively small concentrations for the human body and a leakage from the operating site into other body cavities like the lung can cause fetal outcomes. Another safety aspect of this technique is the over pressure that is built up in the body cavity by the inflated gas. Too high pressure will have a negative effect on circulation in- and around the body cavity. As several systemic vessels pass the Laparoscopic body cavity, a reduction of the circulation in- and around the body cavity can have a dramatic effect on the overall circulation of the body.

When a fluid management system is used the limitation with the volumetric system is that an excessive liquid volume is needed to achieve a rinsing effect. The limitations with the fixed pressure target systems are firstly that it is impossible to flexibly change the pressure depending on the needs during the operation. Thereby an unnecessary high pressure is used in many cases resulting in tissue swelling and subsequently a risk of tissue damage. Secondly the fixed pressure controlled systems seldom operate at the fixed pressure target as the systems are based on the measurement of an indirect pressure in the operation site. When the operation site is drained from liquid it takes some time for such a system to react to a lower pressure due to volume/pressure hysteresis of the tissue, and the reaction time can sometimes be very long resulting in an unnecessarily long time of bad visibility during the endoscopic procedure.

Recently, the inventor herein have developed a novel indirect method, disclosed in US patent publication 20070249993 for irrigation of body cavities under the independent control of pressure and flow through the cavities and depending mainly on the detection of blood cells, red blood cells, haemoglobin and/or debris from the surgical site. The novel methods and devices allow for the detection of the pressure in the body cavity without the introduction of instrumentation for pressure measurement. In the invention the control over the pressure in, and flow through, the surgical site, is achieved by the use of signals from optical sensors provided at a tubing on the outflow site of the body cavity wherein the sensors detect blood cells, red blood cells, haemoglobin and/or debris in the liquid coming out from the surgical site and send signals to a control unit which via a second control unit adjust the inflow liquid pump and/or the outflow liquid device to keep a constant pressure at all times.

With all the aforementioned methods the body cavity expands as a result of the pressure from irrigation or insufflation. Consequently, the higher the body cavity is pressurised, the more distension is accomplished, and subsequently a better view is gained to the surgeon. The drawback is the risk involved with too high pressure settings. If the pressure in the body cavity built up by inflated gas or by irrigated fluids, reach a higher pressure then in the surrounding tissue, vessels or organs potentially tissue damage can occur, with several side effects, which are further discussed below.

Moreover, during the surgical procedure, tissue is surgically treated. For example electro-surgical devices, scissors, tweezers or power tools are used. This normally results in emissions of particles in the operating area such as free tissue, blood cells, boon pieces etc. Emerging free particles obstructs visibility, and it is of course in general desirable to stop distribution of such particulates and moreover to stop bleeding during surgery.

The pressure controlled system according to the known art gives a pressure that has been set by the operator. It will mostly be too high as the operator sets the peek pressure that will be required during the procedure. In the volumetric system the delivered pressure and thereby the pressure in the operating site is unknown. In the pump systems based on US patent publication 20070249993 a better pressure controlled is achieved but the pressure setting is independent on actual pressure in the cavity and it can therefore be adjusted by the system to unnecessary high levels compared to actual needs.

In general the blood flows from the heart by the arterial system to smaller vessels, arterioles, and further into the capillary system. The pressure drops along this liquid pathway. If a vessel in, or in the immediate proximity of the body cavity is broken, the blood will leave the vessel at the point of rupture if the blood pressure in the damaged vessel is higher than in the body cavity, i.e. perfusion pressure is higher than body cavity pressure. The broken vessel would close if the pressure in the body cavity is increased above the perfusion pressure in the vessel, i.e. if the irrigation- or the insufflation pump makes the pressure in the body cavity higher than that of the broken vessel tip. Thus, a properly selected pump pressure, based on the actual perfusion pressure, would hold back the blood from the damaged vessels without over pressurize the operating site. Using this strategy for pressurizing the irrigated saline will also avoid problems with inflow of irrigated saline into the blood stream via the broken vessels. This will lead to a dilution of the blood resulting un-clinical values of several life supporting substances in the blood. This situation is occurring mostly during TUR surgery and has been named TUR Syndrome.

Moreover, in surgeries where the visibility is dependent on flushing of the body cavity with liquid, like TUR, arthroscopy and hysteroscopy, the irrigation pumps also shall maintain an appropriate flow, for rinsing purposes, in combination with the properly selected pressure.

From the visibility point of view and from these last arguments it is concluded that the irrigation pressure and flow through the body cavity delivered by the pump should be as high as possible but should not reach physical dangerous levels.

Nevertheless, in those cases when the pump pressure is too high, tissue damage is likely to occur as a result of that the irrigated liquid or gas goes into other compartments outside the body cavity, into blood vessels and/or into organs. This would put the patient at risk resulting in sever side-effects and lead to death.

A precise control of pressure in the body cavity is therefore of vital importance. It is beneficial to keep the irrigation pressure as low as possible for minimised risk, but as high as possible for best surgical conditions.

Several patent references disclose different approaches to overcome the aforementioned drawbacks and optimize the pressure in the body cavity. Various systems have been proposed in which a combination of endogenous/physiological parameters is used to control a variety of infusion systems.

U.S. Pat. No. 7,510,542, teaches a dual pump irrigation/aspiration pump system capable of operating in a plurality of different modes suitable for a variety of different endoscopic surgical procedures. The system calculates the pressure and adjusts flow to maintain surgeon requested pressure levels at the surgical site while controlling outflow. In a preferred embodiment a pressure control system provides inferred pressure information representative of the pressure at the work site.

US publications 20050126961, and U.S. Pat. No. 6,780,322 disclose a multipurpose hemofiltration system and method for continuously monitoring the flow rates of drained fluid, blood and infusate. A supervisory controller can monitor patient parameters, such as heart rate and blood pressure, and adjust the pumping rates (pump speed) accordingly. The purpose is to provide a linear response or a non-linear (curvilinear) response to the observed changes in the selected monitored parameters.

US 20070055198 refers to a blood volume control method including monitoring a condition of a patient such as hematocrit and automatically adjusting the infusion to maintain the monitored condition at a predetermined value. There are Hct sensors connected to the patients, wherein the sensor generates a control signal for the infusion pump.

US 20080183287 discloses a demand responsive physiological control system for use with a rotatory blood pump; said system including a pump controller which is capable of controlling pump speed of said pump; said system further including a physiological controller, and wherein said physiological controller is adapted to analyze input data relating to physiological condition of the user e.g pulsatile flow, heart rate, and wherein said physiological controller sends a speed control signal to said pump controller to adjust pump speed.

U.S. Pat. No. 5,503,624, relates to an infusion system having a control device for automatically adapting the dosage of drugs to the multi-factorial influences of the patient's condition which can change over time. The system is particularly used for stabilizing the blood pressure during extracorporeal purification of the blood in patients. It is provided with a control device considering a plurality of influence values e.g. plasma volume, hematocrit, pulse, cardiac output per minute and electrolyte concentrations, US 20090069743, Refers to an integrated sensor system for use with an infusion system and include at least one sensor disposed within a catheter. The sensor system may include a sample cell that is in fluid communication with the infusion system, which sample cell may be used with an analyzer to determine a patient's condition. The sensor system may be integrated within a control system for real time monitoring of patient parameters for pump control e.g. via patient fluid analysis.

US 20080262418, teaches an automated therapy system having an infusion catheter, a sensor adapted to sense a patient parameter, and a controller communicating with the sensor and programmed to control flow output from the infusion catheter into a patient based on the patient parameter without removing fluid from the patient. The sensor comprises a blood pressure sensor and the patient parameter is blood pressure. The aim is to control infusion of fluid into patient in order to optimize the therapy being provided. In an embodiment the inventors mention that irrigation and/or lavage of bodily tissues cavities or spaces (or other patient interventions) may be optimized by using a sensors to report pressure or other parameters surrounding the access device in order to automate and optimize the irrigation/lavage.

U.S. Pat. No. 5,800,383, discloses a fluid management system for irrigation of a body cavity and in particular for use in arthroscopic surgery having a pressurized fluid circuit for supplying irrigation fluid and a vacuum fluid circuit for withdrawing waste fluid from the cavity. Some of the features include the monitoring and tracking of cavity pressure and flow rates to predetermined pressure and flow rates, tracking cavity to mean blood pressure, overpressure protection, a plurality of pressure and flow rate baseline settings, monitoring, setting and controlling saline supply, and specialized functions for providing pressure and flow rates for typical surgical procedures such as lavage, clear view, and burr/shaver. The invention discloses means for setting desired cavity pressure manually or automatically in relationship to the patient's blood pressure.

Accordingly, there is a need for a system that deliver fluids or gas during the above-specified endoscopic procedures with as high pressure as needed for the individual patient in a dynamic fashion, thereby avoiding damaging levels but a system that quickly adjust to actual needs during surgery.

Thus, it would from a pressure setting point of view be advantageous to have a system that control the patient's actual perfusion pressure in the body cavity area and adjust delivered irrigation and inflated gas pressure based the patient's individual need.

The present invention satisfies this need and provides related advantages as well.

SUMMARY OF INVENTION

An object of the present invention is to alleviate some of the disadvantages of the prior art and to provide a pressure control device that regulates the pressure of irrigation and/or insufflation in a body cavity during endoscopic procedures in an improved manner.

The invention herein discloses a system comprising a control signal for automatically and dynamically controlling the pressure to be delivered by an irrigation or insufflator pump. Said control signal is derived from a signal from a blood pressure measuring apparatus. The signals are multiplied by a correlation factor, representing the arterial pressure in relation to the perfusion pressure in blood vessels surrounding the body cavity, e.g. in the operating site. The resulting control signal follows the varying blood pressure throughout the surgical procedure and controls the pump to deliver fluids with an optimal pressure, i.e. a combination of a safe pressure level, that do not extend actual pressure in the surrounding blood vessels of the body cavity, and an efficient pressure so that blood leakage from damaged blood vessels will not leak into the operating site.

The overall aim of the present invention is to keep the irrigation and gas pressure as low as possible to minimize tissue damage caused by excessive tissue distension or liquid/gas loss into adjacent tissue, but as high as possible for best view, as the surgical area is made visible by pressurisation of the body cavity with irrigation liquid or gas. To obtain an efficient pressure level in the body cavity the pump therefore will deliver a pressure equal to the perfusion pressure adjusted with a factor so that the pressure in the body cavity is just above the perfusion pressure. The factor is different from body cavity to body cavity and is chosen by the operator of the pump when the surgery type is selected.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

In a first aspect there is provided a device for irrigation and/or insufflation during endoscopic surgery/procedures in a body cavity, comprising
- a first fluid pump device in fluid connection with the body cavity via a fluid line, wherein first fluid pump device adapted to deliver a fluid to the body cavity on an inflow side of the body cavity
- a second fluid pump device in fluid connection with the body cavity connected via a fluid line, wherein the second fluid pump device is adapted to move a fluid from the body cavity on an outflow side of the body cavity,
- a control unit connected to the first fluid pump device,
- a blood pressure measuring device, connected to the control unit
- wherein the control unit is adapted to derive a control signal based on a signal from the blood pressure measuring device, wherein the control unit is further adapted to send the control signal to the first fluid pump device, wherein the control signal is derived by multiplying the signal from the blood pressure measuring device with a correlation factor stored in the device wherein the correlation factor is dependent on the known relationship between a blood pressure measurement signal, and a perfusion pressure of the body cavity.
- wherein the first fluid pump device is adapted to control the pressure in the body cavity based on said control signal received from the control unit.

According to one embodiment, the control signal is derived by multiplying the signal from the blood pressure measuring device with an adjustment factor stored in the device corresponding to a preferred required over pressure above the perfusion pressure of the body cavity.

According to one embodiment, the control signal is derived by multiplying the signal from the blood pressure measuring device with a compensation value stored in the device corresponding to the height level difference between the position for blood measurement and the body cavity.

According to one embodiment, a first fluid pressure measuring device is arranged to measure a deliver pressure, corresponding to the pressure of the fluid delivered to the body cavity on the inflow side of the body cavity.

According to one embodiment, a second fluid pressure measuring device is arranged to measure the pressure of the fluid leaving the body cavity on the outflow side of the body cavity, wherein the second fluid pressure measuring device is connected to the control unit, wherein the control unit is further adapted to receive a fluid pressure measurement signal from the second fluid pressure measuring device and adjust the control signal based on said fluid pressure measurement signal.

According to one embodiment, the second fluid pressure measuring device is adapted to measure the pressure of the fluid on the outflow side of the body cavity after a certain time period has passed since the second fluid pump device has been set in an non-operating mode whereby the second fluid pump device has stopped moving fluid from the body cavity.

According to one embodiment, the second fluid pressure measuring device is adapted to measure the pressure of the fluid on the outflow side of the body cavity in one measurement and/or in several measurements under a time period whereby the mean fluid pressure is calculated.

According to one embodiment, the blood pressure measuring device comprises any one of a non-invasive blood pressure meter, an invasive blood pressure meter signal, or a monitoring equipment associated to endoscopic surgery or procedures.

According to one embodiment, the blood pressure measuring device is integrated in the device or is a separate external module.

According to one embodiment the control unit is connected to the second fluid pump device.

According to one embodiment, the control unit is adapted to control respectively the first and second fluid pump devices to control the irrigation/insufflation pressure in the body cavity.

According to one embodiment, a method is provided for controlling the irrigation or insufflation fluid pressure in a body cavity, comprising the steps:
  setting a default target deliver pressure (DP-dt) for the irrigation or insufflation fluid,
  measuring the systemic blood pressure of a patient comprising the body cavity,
  dynamically calculating a true perfusion pressure (PP-t) based on the measured systemic blood pressure,
  automatically adjusting the default target deliver pressure (DP-dt) based on the true perfusion pressure (PP-t) into an actual target for the deliver pressure (DP-at).

According to one embodiment, the default target deliver pressure (DP-dt) corresponds to the normal perfusion pressure (PP-n) in the specific body cavity plus an adjustment factor (A) of 5-15% depending on the specific body cavity to prevent bleeding in the specific body cavity.

According to one embodiment. the method further comprises automatically adjusting the default target deliver pressure (DP-dt) into the actual target for the deliver pressure (DP-at) comprises:
  calculating (PP-t+A) and comparing with (DP-dt),
  increasing or decreasing (DP-dt) into (DP-at) if (PP-t+A) deviates from (DP-dt).

According to one embodiment, the method further comprising setting the second fluid pump device in a non-operating mode whereby the second fluid pump device stops moving fluid from the body cavity, measuring the pressure of the fluid leaving the body cavity after a certain time period has passed since the second fluid pump device has been set in an non-operating mode, comparing (DP-at) with pressure of the fluid leaving the body cavity, which then equal actual body cavity pressure after adjustment of resistance in fluid pathway, adjusting (DP-at) if deviates from the pressure of the fluid leaving the body cavity.

According to one embodiment, the method further comprising: providing a warning signal if (DP-at) deviates significantly from the pressure of the fluid leaving the body cavity, whereby significantly comprises more than >10%, which indicates leakage of liquid from the fluid pathway.

According to one embodiment, the method further comprising the step: continuously delivering a fluid deliver pressure to the body cavity according to (DP-at).

According to one embodiment, the actual target for the deliver pressure (DP-at) is dynamically adjusted regularly based on the measured systemic blood pressure.

According to one embodiment, the actual target for the deliver pressure (DP-at) is dynamically adjusted regularly every 2-5 seconds based on the measured systemic blood pressure.

According to one embodiment, the method further comprising the step of pressurizing the irrigation or insufflation fluid using a first fluid pump device according to any embodiments herein describing such first fluid pump device, comprising at least first fluid pump devices as described in [0036]-[0054] above.

According to one embodiment, there is provided a device for irrigation and/or insufflation during endoscopic surgery/procedures in a body cavity, comprising
  a first fluid pump device in fluid connection with the body cavity via a fluid line, wherein the first fluid pump device is adapted to deliver a fluid to the body cavity,
  a second fluid pump device in fluid connection with the body cavity via a fluid line, wherein the second fluid pump device is adapted to move a fluid from the body cavity,
  a control unit connected to the first fluid pump device and/or the second fluid pump device,
  a blood pressure measuring device, connected to the control unit, wherein the blood pressure measuring device is adapted to measure a blood pressure, e.g. a systemic blood pressure,
  wherein the control unit is adapted to derive a control signal based on a signal from the blood pressure measuring device, wherein the control unit is further adapted to send the control signal to the first fluid pump device and/or the second fluid pump device, wherein the control signal is derived by processing the signal from the blood pressure measuring device by using a correlation factor stored in the device wherein the correlation factor is dependent on the relationship between a blood pressure measurement signal, and a perfusion pressure of the body cavity.
  wherein the first fluid pump device and/or the second fluid pump device is adapted to control the pressure in the body cavity based on said control signal received from the control unit.

According to one embodiment, the correlation factor is a product of the relationship between a blood pressure measurement signal, and a perfusion pressure of the body cavity.

According to one embodiment, the control signal is derived by processing the signal from the blood pressure measuring device by using an adjustment factor stored in the device corresponding to a preferred required over- or under pressure versus the perfusion pressure of the body cavity.

According to one embodiment, the control signal is derived by processing the signal from the blood pressure measuring device by using a compensation value stored in the device corresponding to the height level difference between the position for blood measurement and the body cavity.

According to one embodiment, a first fluid pressure measuring device (22) is arranged to measure a deliver pressure Pi, corresponding to the pressure of the fluid delivered to the body cavity.

According to one embodiment, the control unit is adapted to calculate an estimated pressure Pei in the body cavity based on the measured deliver pressure Pi, the static pressure difference between the body cavity and the pressure at the first fluid pressure measuring device Ph, and a pressure drop Pdi in the fluid line between the first fluid pressure measuring device and the body cavity, wherein the control unit is further adapted to compare the control signal which corresponds to an actual target for the deliver pressure DP-at, with the estimated pressure Pei and adjust the first fluid pump device and/or the second fluid pump device to bring Pi to a pressure such that Pei=DP-at.

According to one embodiment, a second fluid pressure measuring device is arranged to measure the pressure of the fluid leaving the body cavity, wherein the second fluid pressure measuring device is connected to the control unit, wherein the control unit is further adapted to receive a fluid pressure measurement signal from the second fluid pressure measuring device and adjust the control signal based on said fluid pressure measurement signal.

According to one embodiment, the control unit is adapted to calculate an estimated pressure Peo in the body cavity based on the measured pressure of the fluid leaving the body cavity Po, the static pressure difference between the body cavity and the pressure at the first fluid pressure measuring device Ph and/or the second fluid pressure measuring device, and a pressure drop Pdo in the fluid line between the body cavity and the second fluid pressure measuring device, wherein the control unit is further adapted to compare Peo with Pei and trigger a corrective action if the difference between Peo and Pei is greater than a threshold value, wherein the threshold value is e.g. >10%

According to one embodiment, the second fluid pressure measuring device is adapted to measure the pressure of the fluid leaving the body cavity after a certain time period has passed since the second fluid pump device has been set in an non-operating mode whereby the second fluid pump device has stopped moving fluid from the body cavity.

According to one embodiment, the second fluid pressure measuring device is adapted to measure the pressure of the fluid leaving the body cavity in one measurement and/or in several measurements under a time period whereby the mean fluid pressure is calculated.

According to one embodiment, the blood pressure measuring device comprises any one of a non-invasive blood pressure meter, an invasive blood pressure meter signal, or a monitoring equipment associated to endoscopic surgery or procedures.

According to one embodiment, the blood pressure measuring device is integrated in the device or is a separate external module.

According to one embodiment, processing the signal from the blood pressure measuring device by using a correlation factor stored in the device comprises or is defined by multiplying the signal from the from the blood pressure measuring device with the correlation factor stored in the device.

According to one embodiment, a method is provided for controlling the irrigation or insufflation fluid pressure in a body cavity, comprising the steps:
  setting a default target deliver pressure (DP-dt) for the irrigation or insufflation fluid,
  measuring the blood pressure, e.g. the systemic blood pressure, of a patient comprising the body cavity,
  dynamically calculating a true perfusion pressure (PP-t) based on the measured blood pressure by processing a signal from the blood pressure measuring device by using a correlation factor,
  automatically adjusting the default target deliver pressure (DP-dt) based on the true perfusion pressure (PP-t) into an actual target for the deliver pressure (DP-at).

According to one embodiment, the default target deliver pressure (DP-dt) corresponds to the normal perfusion pressure (PP-n) in the specific body cavity (3) plus an adjustment factor (A) of 5-15% depending on the specific body cavity (3) to prevent bleeding in the specific body cavity.

According to one embodiment, automatically adjusting the default target deliver pressure (DP-dt) into the actual target for the deliver pressure (DP-at) comprises:
  calculating (PP-t+A) and comparing with (DP-dt),
  increasing or decreasing (DP-dt) into (DP-at) if (PP-t+A) deviates from (DP-dt).

According to one embodiment, the method further comprising
  setting a second fluid pump device in a non-operating mode whereby a second fluid pump device (18) stops moving fluid from the body cavity.
  measuring the pressure of the fluid leaving the body cavity after a certain time period has passed since the second fluid pump device has been set in an non-operating mode,
  comparing (DP-at) with pressure of the fluid leaving the body cavity, adjusting (DP-at) if deviates from the pressure of the fluid leaving the body cavity According to one embodiment, the method further comprising
  providing a warning signal if (DP-at) deviates significantly from the pressure of the fluid leaving the body cavity, whereby significantly comprises more than >10%.

According to one embodiment, the method further comprising the step continuously delivering a fluid deliver pressure to the body cavity according to (DP-at).

According to one embodiment, the method further comprising the steps:
  measuring the deliver pressure Pi, corresponding to the pressure of the fluid delivered to the body cavity,
  determining a static pressure difference between the body cavity and the pressure at a first fluid pressure measuring device Ph,
  determining a pressure drop Pdi in the fluid line between the first fluid pressure measuring device Ph and the body cavity
  calculating Pei=Pi−Ph−Pdi,
  comparing Pei with the actual target for the deliver pressure (DP-at),
  adjusting Pi such that Pei=(DP-at).

According to one embodiment, the method further comprising the steps:
  measuring the pressure of the fluid leaving the body cavity Po,
  determining the static pressure difference between the body cavity and the pressure at the first fluid pressure measuring device and/or the second fluid pressure measuring device Ph,
  determining a pressure drop Pdo in the fluid line between body cavity and the second fluid pressure measuring device,
  calculating Peo=Po−Ph+Pdo
  comparing Peo with Pei
  triggering a corrective action if the difference between Peo and Pei is greater than a threshold value, wherein the threshold value is e.g. >10%, According to one embodiment, the actual target for the deliver pressure (DP-at) is dynamically adjusted regularly based on the measured blood pressure, e.g. measured systemic blood pressure.

According to one embodiment, the actual target for the deliver pressure (DP-at) is dynamically adjusted regularly every 2-5 seconds based on the measured blood pressure, e.g. systemic blood pressure.

According to one embodiment, the method further comprising the step of pressurizing the irrigation or insufflation fluid using a first fluid pump device according to any embodiments herein describing such first fluid pump device, comprising at least first fluid pump devices as described in [0056]-[0078] above.

According to one embodiment, processing the signal from the blood pressure measuring device by using a correlation factor stored in the device comprises or is defined by multiplying the signal from the from the blood pressure measuring device with the correlation factor stored in the device.

BRIEF DESCRIPTION OF DRAWINGS

The invention is now described, by way of example, with reference to the accompanying drawings, in which.

DESCRIPTION OF EMBODIMENTS

Figure 1:
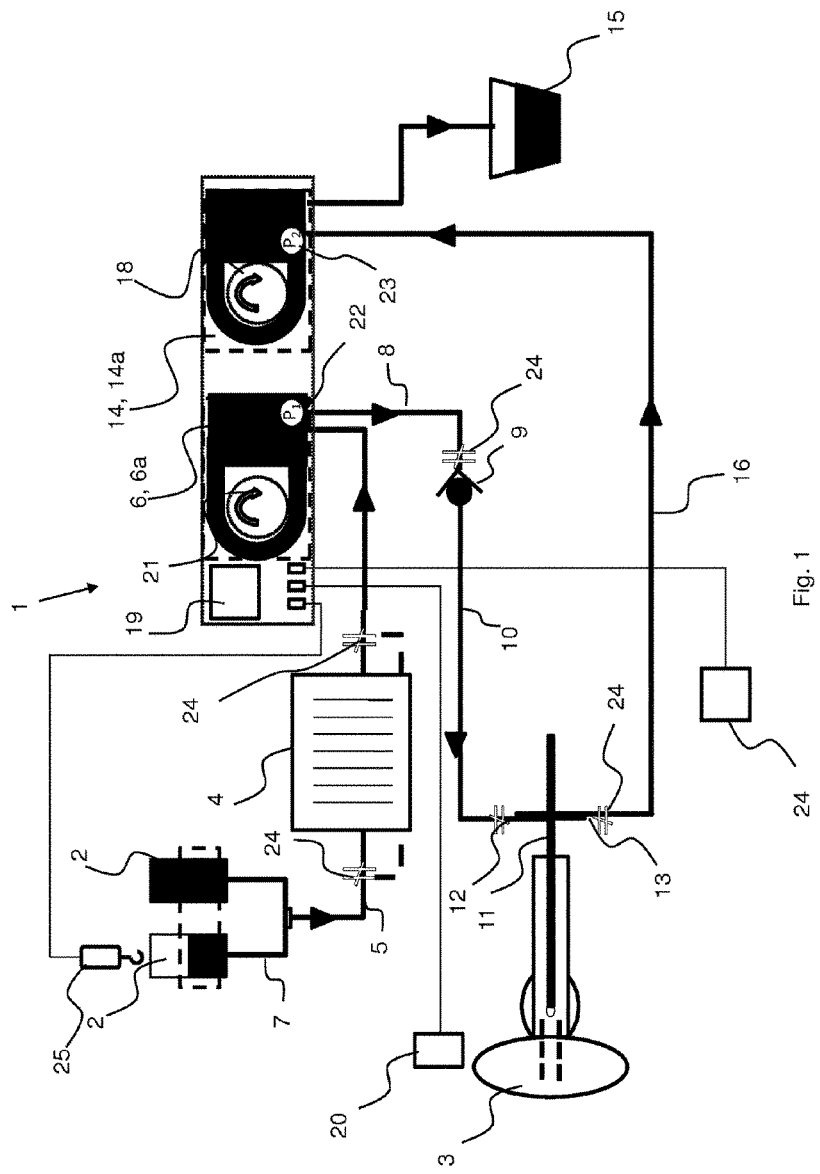
FIG. 1 shows a device for irrigation and/or insufflation during endoscopic surgery/procedures in a body cavity

In the following, a detailed description of the invention will be given. In the drawing figures, like reference numerals designate identical or corresponding elements throughout the several figures. It will be appreciated that these figures are for illustration only and are not in any way restricting the scope of the invention.

According to one embodiment, an improved way for optimising the pressure in the body cavity is to irrigate/flush it with a pressure that is just over the perfusion pressure in the blood vessels by the body cavity. The perfusion pressure is very individual, and often is lowered as a result of anaesthesia used during the surgery, if used. It may change substantially over the time of a procedure.

Before explaining each embodiment in detail it has to be underlined that the present invention is not limited to TUR or Laparoscopy, but any endoscopic procedure that pressurizes a cavity in the body of a human or animal. For instance, this invention is beneficial in arthroscopy applications. In this example the endoscopically viewed area is the joint.

According to one embodiment, the present invention can be carried out using a double peristaltic roller type pump, as disclosed in US patent publication 20070249993. Thus, the body cavity is irrigated with a clear liquid by means of a pump referred as an inflow liquid pump. Similarly the liquid from the body cavity is removed by means of a second pump or other suction source referred to as an outflow liquid pump. Both functions are integrated in a single device.

Briefly, Blood pressure (BP) is the pressure exerted by circulating blood upon the walls of blood vessels and is one of the principal vital signs. During each heartbeat, BP varies between a maximum systolic and a minimum diastolic pressure. The blood pressure in the arterioles by the body cavity is directly correlated to the blood pressure in the artery of the upper arm. Blood pressure is commonly measured non-invasively by compressing the upper arm with a cuff, and the systolic blood pressure is that of the air pressure in the cuff if blood only just can pass by under the cuff. The blood pressure can then be measured by correlating to the air pressure in the cuff. This method is simpler and quicker than invasive measurements in which a catheter is placed in a blood vessel. The catheter is hydraulically connected to a blood pressure transducer, signalling the blood pressure to an electrical amplifier and a further to blood pressure monitoring apparatuses. The advantage of this system is that pressure is constantly monitored beat-by-beat, and a waveform (a graph of pressure against time) can be displayed. As a third possibility, blood pressure can be correlated to that of the air pressure in a cuff placed over a finger.

In this regard it should be noted that this invention is not limited to control of the systolic or diastolic blood pressures in the upper arm. For instance—in the urology procedure to resect and remove the prostate gland via the urethra, the bleeding is related to the blood pressure of the venous system in the prostate. The prostate gland has a very dense vasculature. The blood pressure here is much below diastolic blood pressure in the upper arm, and the irrigation pressure control can very beneficially be controlled by the blood pressure that correlates to the venous system in the prostate gland. The pressure in the venous system of the body that correlates to the blood pressure in the venous system of the prostate gland may be measured with a cuff and a oscillometry principle method to measure blood pressure. In conjunction with an ultrasound Doppler, the venous blood pressure can be measured on the calf of the patient. The venous blood pressure can also—for instance—be measured invasively with a tip transducer or by a catheter that is connecting the vessel to an external blood pressure transducer. The detected venous blood pressure is then related to the blood pressure in the venous vascular system of the prostate by a correlating factor and also by a compensation value being the different level of the site where the venous blood pressure is measured, and the prostate gland. The latter is 10 mmHg per 13 cm of level difference. This function not only gains restriction of blood emerging to the bladder, but also minimises risk of irrigation liquid entering the blood vessels. The latter addresses one of the most critical hazards in Trans Urethral Resectomy (TUR), and is a most beneficial solution to a fundamental and well known risk of Trans Urethral Resectomy in general.

According to one embodiment, a novel system is put forth comprising a control signal for automatically and dynamically controlling the pressure to be delivered by an irrigation pump. Said control signal is derived from a signal from a blood pressure measuring apparatus or device, such as a common non-invasive blood pressure meter, an invasive measurement signal from a pressure transducer with the relevant signal amplifier, or a signal from monitoring equipment associated to surgical procedures or other apparatus for measuring the blood pressure. These signals may alternatively be derived from a blood pressure sensing module integrated in the pump system cabinet, or as an external separate module; in connection with the pump system. A Control Unit in the pump system collect the signals and multiply it by a correlation factor, representing the upper arm mean systole and diastole pressure in relation to the pressure in vessels by the body cavity, giving a factor that represent the actual perfusion pressure in the vessels surrounding the body cavity. The factor is different between the body cavities. As an example a TUR operation of the prostate (TUR-P) result mainly in bleeding from veins. Consequently the factor when TUR-P surgery has been selected as operation mode for the pump system will give a calculated perfusion pressure that equals to diastole pressure (i.e. pressure in the veins). The Control Unit adjust the factor and based on that control the pump system's delivery pressure so that an optimal body cavity pressure is obtained. The adjustment of the factor is done based on what is known as required over pressure (i.e. extra pressure vs. the perfusion pressure) in the body cavity to obtain optimal surgical conditions. In summary the resulting control signal tracks the varying blood pressure throughout the surgical procedure and controls the irrigation pump to provide an optimal pressure in the body cavity.

Essential for the function of the innovation herein described is to know the actual body cavity pressure that is obtained by the pump system. Pumps system used in Endoscopic surgery mainly measure the deliver pressure. Some devices calculated the actual body cavity pressure based on the measured deliver pressure and then take into consideration the resistance in irrigation system. The drawback of this method is that body cavities has different uptake of the irrigated fluids, described as the body cavity compliance. Even if the pressure of the irrigated fluids at the point of delivery into the body cavity has been calculated this information cannot be used as the true pressure in the body cavity It is therefore important when selecting the optimal irrigated pressure to calculate the resistance in the irrigation system and also the compliance in the body cavity. The resistance and the compliance shall be analyzed during routine use of the pump system. This can be done via two pressure devices, one on the delivery side and one on the outflow side. In a situation when the pressure is high at the inflow side and lower at the outflow side the compliance in the body cavity has decreased the pressure.

The pump system herein described will calculated the body cavity pressure based on the measured delivery pressure, measured on the inflow side; compensate this number with factors for irrigation system resistance and factors for known body cavity compliance. By measure the actual pressure on the outflow side the pump system will control that the adjusted irrigation pressure is sufficiently to compensate for actual resistance and compliance.

The optimal pressure to be provided to the body cavity is also dependent of other factors. For instance, a key factor to consider is the difference in height between the irrigation pump and the surgical cavity, which results in a pressure loss or gain. If the irrigation pump is placed below the surgical cavity, then the pressure will be lower in the surgical cavity as an effect of gravity on the irrigation liquid. By introducing the height of the pump in relation to the surgical cavity, the resulting pressure change can be compensated for.

The above-mentioned flow/pressure relationship is discussed with a constant flow in mind. If one should take not only a constant static flow into account but also the change in flow, the flow restriction in the tubing and instrumentation is described as impedance. Further, and of importance, is the reactive component of the impedance. The reactance can also be explained as the inertia of the liquid in the line and instrumentation: Is the liquid is accelerated, the acceleration needs some energy in itself, and this may further be dependent of the construction of the irrigation system and its hydraulic characteristics.

The reactive component of the impedance has a restrictive effect on acceleration of the liquid in the tubing and instrumentation. The consequence is that an initiated change of pressure results in a change of flow after some time. At a nominal pressure and nominal flow for an endoscopy system as described, this flow change is approximately 2 seconds. For utmost control of pressure in the body cavity, this reactance must be taken into account. The decision to increase flow is as a rule fairly urgent. Thus, the pressure that accelerates the liquid has to initially be even higher than the designated pressure by the inflow pump to accelerate the liquid. This can be defined as an overpressure. As the flow is to be increased, the reactive component is compensated for by the overpressure. The reactive component has to be established for various instrument setups as well as the resistance mentioned earlier in this patent application. Also, the flow away from the body cavity can optionally be delayed by introducing a delay of the start of the outflow pump to further enhance a rapid increase in pressure. Alternatively, the outflow pump may increase rotational speed with more or less acceleration, as it takes some time to introduce the elevated pressure in the body cavity. Further, if the rinsing is too intense, the inflow may not be able to provide the necessary flow due to the reactance and resistance in the inflow line. It may be necessary to make a decision if the pressure or rinsing has the highest priority. The user can make this decision by the use of a software program or by a manual selection. The software decision can be made on a basis of the compliance calculation mentioned above. The manual selection can be a front panel switch with selection of procedure type "urine bladder" etc.

In yet another situation, the compliance of the body cavity may be very high. In the case of rinsing an irrigated pressurized body cavity, there may be an elevated outflow but the system would not replace the liquid by maintaining the pressure as described above. Pressure would nearly persist, but the liquid volume in the body cavity would drop. Technically speaking, this is a description of tissue hysteresis, originating from the fact that more force is needed from the pressurized liquid to expand tissue surrounding the body cavity than is needed to maintain the body cavity volume. In this particular situation, the viewing field will eventually diminish as the body cavity "caves in". The reason for this is that residual pressure inhibits a relevant inflow to replace the removed liquid. The inflow pump pressure regulation detects a relatively high pressure, as the body cavity is collapsing and the volume drops. When this particular situation is the case, the system may decide to elevate the speed of the inflow pump to that of the outflow pump to compensate for the drawn liquid. The system must however constantly monitor the pressure, as this may not be elevated too high. The afore-mentioned solution of maintaining the viewing area by replacing drawn liquid with the inflow pump with only careful influence of pressure in the body cavity is very advantageously.

As can be seen in FIG. 1, according to one embodiment, a device 1 for irrigation and/or insufflation during endoscopic surgery/procedures in a body cavity 3 is provided, comprising a dual urology pump system intended to provide irrigation during transurethral resection surgery and thereby obtain cavity distension and rinsing during the procedure.

According to one embodiment, the device 1 for irrigation and/or insufflation during endoscopic surgery/procedures in a body cavity 3 provides liquid irrigation and aspiration/evacuation during transurethral resection (TUR) surgery. The device (1) comprises two individual roller pumps, or fluid pump devices 21, 18, one for irrigation/insufflation and one for outflow. Both roller pumps/fluid pump devices 21, 18 are software controlled and automatically manage flow and deliver-pressure, i.e. the pressure the irrigated liquid has when delivered into the operating site. The deliver pressure level is based on actual procedure settings, chosen by the user, and actual pressure requirement during surgery. The pressure requirement is established from measurement of actual systemic blood pressure. The blood pressure is measured by a blood pressure device 20, separate or integrated into the device 1. If needed, both flow and pressure settings can also be individually adjusted by the operator via a foot pedal 24, wire- or wireless connected to the pump 21, 18 or device 1.

The irrigated/insufflated fluid is heated via a separate heating device 4 which is part of the device 1. According to one embodiment, the heating device 4, the is a stand-alone unit which has the purpose of; (i) holding the fluid bags 2, (ii) alarm pump and users when the bag 2 is finished and (iii) heat up the fluids when it is flushed into the irrigation side of the device 1. According to one embodiment, a empty bag indicator 25 is provided and connected to the a control unit 19 for sending indication signal indicating a user when the bag is empty/finished.

According to one embodiment, the irrigation and/or insufflation system or device 1 deliver fluids from a separate fluid bag 2 to the operating site/body cavity 3 through the irrigation side of the device 1 and then evacuate or move it via the outflow side of the device 1. A heater device 4 is connected to the fluid bag 2 and transports the fluids to and from the heater device 4. During the passage through the heater device 4, the fluid can be heated to 25-40° C., stepwise chosen by the user. The inflow (proximal) tube 5 in a first cassette 6, also referred to as day cassette 6, is connected to the tube 7 coming from the heater device 4, which transport the fluids to the cassette house 6a on the irrigation/insufflation side of the device 1. Flow through the cassette house 6a is obtained by a peristaltic movement of the fluids created by a first pump wheel of a first fluid pump device 21 that pressurize the pump wheel tube that is part of the cassette house 6a. According to one embodiment, on the distal end of the pump wheel, in the cassette house 6a, measurement of fluid pressure is made by two independent pressure transducers. According to one embodiment, the fluid pressure is made by one pressure transducer. The pressurized fluid moves out from the cassette house 6a and into the outgoing tube 8 from the cassette house 6a. In the outgoing tube 8 it passes a back-valve 9, which prevents fluids to go back to the cassette house 6a. The inflow tube 10 of the device 1 is connected to the outgoing tube 8 in the distal end of the valve 9. According to one embodiment, the inflow tube 10 transports the fluid approx. 2 meters and when the inflow tube 10 is connected to inflow port 12 of the endoscope 11, further into the body cavity/operating site 3. According to one embodiment the device 1 comprises luer lock connection devices denoted by references 24 in FIG. 1.

According to one embodiment, the fluids are evacuated from the body cavity/operating site 3 via the endoscope 11 and its outflow port 13. The irrigation and/or insufflation system 1 second cassette/patient Cassette tube 16 is connected to this port 13. The fluid is drained out through an under pressure in the tube created by a second pump wheel of a second fluid pump device 18 on the outflow side of the device 1. When the fluid has passed the second pump wheel, via the cassette house tube that is tightly positioned over the pump wheel, it is forced out from the cassette house 14a by the overpressure that is created by the pump wheel into a waste bag 15 or similar.

According to one embodiment, when the fluid is delivered into the cavity 3 it has a certain pressure, i.e. the deliverpressure (DP). The device 1 operates with a specific DP that is a product of several parameters. Firstly, the choice of procedure, chosen by the operator when starting the device 1, set a default target (DP-dt). The default target equals the normal perfusion pressure (PP) in the cavity 3, i.e. the blood pressure in the blood vessels in the cavity 3 and surrounding tissue, plus an adjustment (A) of 5-15% overpressure, depending on cavity 3, to prevent bleeding in the cavity/operating site 3. Secondly, the device 1 measured the systemic blood pressure for the patient under surgery, i.e. the patient comprising the body cavity 3, and dynamically calculates the true PP (PP-t) during the procedure. If (PP-t+A) deviates from DP-dt the device 1 automatically adjust DP-dt to meet the true pressure requirement. The new target for the DP becomes the actual target for the deliver pressure (DP-at). DP-at is dynamically adjusted every 2-5 seconds when the device 1 has on-line systemic blood pressure information available. If this information is not available or the device 1 determines the information to be inaccurate, the pump uses the DP-dt as its DP-at.

According to one embodiment, the device 1 establishes a deliver pressure from measured pressure in the first cassette 6. The measured pressure is adjusted for resistance in and length of the fluid pathway into the cavity 3 and for normal cavity compliance.

During the operation the device 1 controls that the deliver pressure is accurate with the required pressure in the cavity 3, i.e. the DP-at. This is done through measurement of the pressure in the outflow tubing 16 connected to the endoscope 11 using a second pressure measuring device 23 when the second pump/evacuation pump 18 is in stand-by mode, i.e. the true DP-at. According to one embodiment, the second fluid pressure measuring device 23 is adapted to measure the pressure of the fluid on the outflow side of the body cavity 3 after a certain time period has passed since the second fluid pump device 18 has been set in an non-operating mode whereby the second fluid pump device 18 has stopped moving fluid from the body cavity 3.

The measurement of true DP-at is regular performed during the procedure in an automatically software driven way or manually, when the operator likes to control the DP-at vs. true DP-at. The manual operation is activated via the foot pedal 24. If the true DP-at do not correspond with DP-at the device 1 adjust the target level and a new DP-at is obtained.

Figure 2:
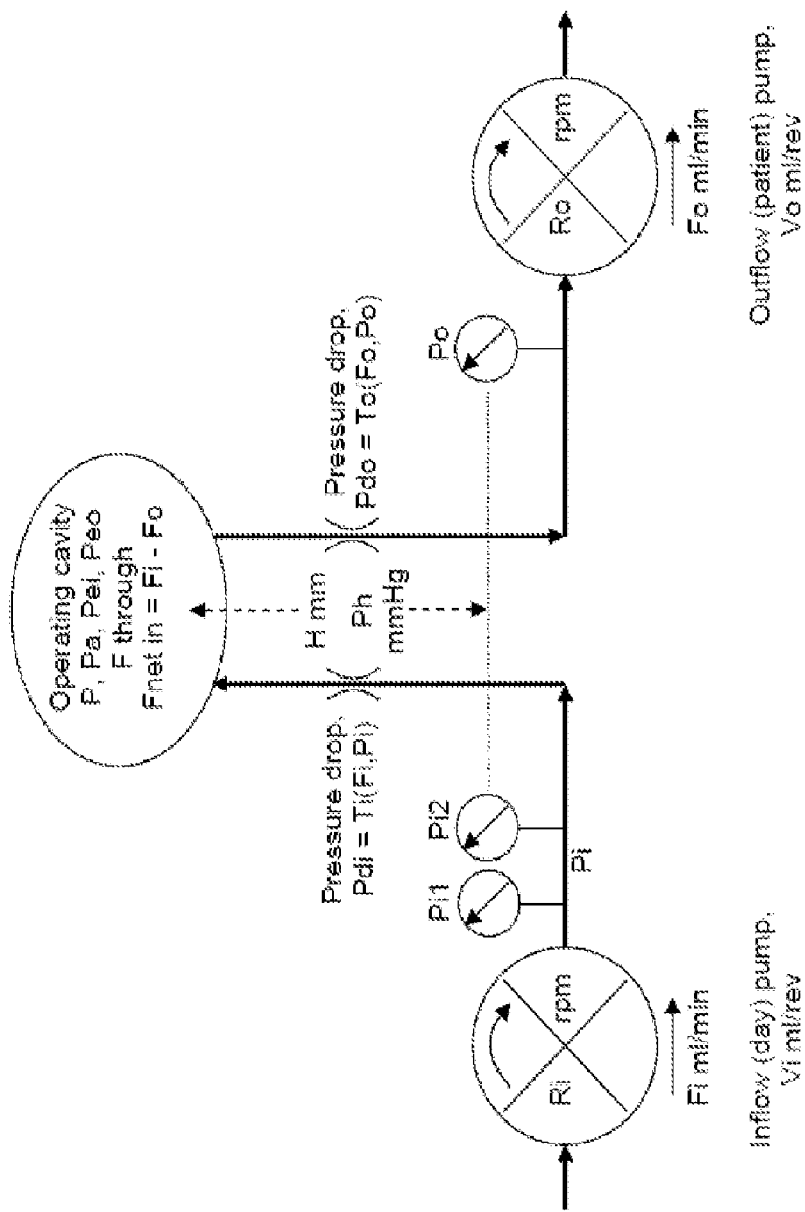
FIG. 2 shows a functional diagram of the device for irrigation and/or insufflation during endoscopic surgery/procedures in a body cavity

According to one embodiment, with reference to FIG. 2, the following abbreviations may be used to describe the embodiment;

Fi (in ml/min)=flow rate at inflow (day) pump.
Ri (in revs/min)=rotational speed of inflow (day) pump.
Vi (in ml/rev)=volume delivered per rev of inflow (day) pump. This depends on tube size. There is a small effect of pressure, which may be negligible or may be included in the calculations.
Pi (in mmHg)=inflow pressure=pressure downstream of inflow (day) pump=average of 2 readings of pressure (Pi1 and Pi2) made by two independent pressure sensors in day cassette=(Pi1+Pi2)/2
Fo (in ml/min)=flow rate at outflow (patient) pump
Ro (in revs/min)=rotational speed of outflow (patient) pump.
Vo (in ml/rev)=volume delivered per rev of outflow (patient) pump. This depends on tube size. There is a small effect of pressure, which may be negligible or may be included in the calculations.
Po (in mmHg)=outflow pressure=pressure upstream of outflow (patient) pump
F (in ml/min)=target flow rate through operating cavity, set by flow state.
P (in mmHg)=target pressure in operating cavity, set by flow state.
Fnet (in ml/min)=net flow rate into operating cavity=(Fi−Fo).
H (in mm)=height difference between operating cavity and inflow and outflow pressure sensors=(height from floor to operating cavity)−(height from floor to instrument pressure sensors). Note: Inflow and outflow pressure sensors will be at same height. H is positive when operating cavity is higher than instrument.

Ph (in mmHg)=static pressure difference between pressure in operating cavity and pressure at height of inflow and outflow pressure sensors, due to height difference=H×density of irrigation fluid/density of Hg=H×1,004.6/13,579 (assuming fluid is saline at 9 grams NaCl per liter H20 at 22° C. and Hg is at 20° C.)=0.074×H. Note that if a typical value of H in an operating theatre is 500 mm (=0.5 m, eg. ENDO pump at 0.6 m and patient at 1.1 m), then Ph would be 37 mm Hg. Kidney procedures normally need P=40 mmHg and TUR-P need 60 mmHg, so a Ph of 37 mmHg is a significant factor in controlling the P in the operating cavity. If Ph was ignored and taken as 0, the pressures in the operating cavity would be 37 mmHg lower than expected (if H is 500 mm).
Pdi (in mmHg)=pressure drop in inflow tubes and endoscope inlet=Ti (Fi, Pi). This is a function of Fi and Pi and may depend of what endoscope is being used. The function can be characterised in advance and can be treated as known.
Pdo (in mmHg)=pressure drop in endoscope outlet and outflow tubes=To (Fo, Po). This is a function of Fo and Po and may depend of what endoscope and what tube that is being used. The function can be characterised in advance and can be treated as known.
When the flow is working normally, without blockages, the system gives two independent estimates of the pressure in the operating cavity:
Pei (in mmHg)=estimated pressure achieved in operating cavity, using inflow conditions, given by:

$$Pi=(Pei+Ph)+Pdi, \text{ so}$$

$$Pei=Pi-Ph-Pdi=Pi-Ph-Ti(Fi,Pi).$$

Peo (in mmHg)=estimated pressure achieved in operating cavity, using outflow conditions,
given by:

$$Po=(Peo+Ph)-Pdo, \text{ so}$$

$$Peo=Po-Ph-+Pdo=Pi-Ph+To(Fo,Po).$$

In normal conditions, Pei and Peo are equal and give the actual pressure in the operating cavity:
Pa (in mmHg)=actual pressure achieved in operating cavity=Pei=Peo.

According to one embodiment, the measurements that will be made in real time are:
Ri Measured from inflow pump-head or motor.
Pi1 Measured from inflow pressure sensor 1, after it has been calibrated.
Pi2 Measured from inflow pressure sensor 2, after it has been calibrated.
Ro Measured from outflow pump-head or motor.
Po Measured from outflow pressure sensor, after it has been calibrated. The parameters that will be known from configuration are:
Vi From inflow pump-head tubing.
Ti From inflow tubing and endoscope type.
Vo From outflow pump-head tubing.
To From outflow tubing and endoscope type.
The parameters that will need to be determined are:
H This could be entered by user, alternatively means to determine it may be provided According to one embodiment, the measurements made in real time will be used with the known parameters to do the following calculations:
1. Both pumps will have demand speeds limited to 600 ml/min by software. If demand exceeds 600 ml/min under any conditions, it will be clamped at 600 ml/min.
2. If DC motors are used on the pumps, run real-time PID control loops on the inflow and outflow pump motors, to achieve the exact flow rates that are demanded, regardless of how much current or torque is required, but subject to a torque limit that indicates pump is jammed in a fault condition. If stepper motors are used on the pumps, run motors with step rates and phase currents that achieve the exact flow rates that are demanded. Use feedback from encoders to check that the required motor speed is being achieved, without steps being lost due to jams, insufficient torque or resonances. When step rates need to increase or decrease, use ramps if this useful to get best performance, or immediate changes in rate if ramps are not useful. With stepper motors, it is possible that different modes will be used at low and high speed (eg. micro-stepping at slow speeds and half-stepping at high speeds).
3. Compare Pi1 and Pi2 and confirm that pressure sensors are in agreement. If difference is too great trigger an error or warning.
4. Calculate Pei using:

$$Pei=Pi-Ph-Pdi=(Pi1+Pi2)/2)-(k\times H)-Ti(Fi,Pi).$$

Compare Pei to target pressure P and adjust inflow pump flow rate as discussed below using closed loop control to bring Pi to pressure that makes Pei=P.
5. Calculate Peo using:

$$Peo=Po-Ph+Pdo=Po-(k\times H)+To(Fo,Po).$$

Compare Peo to Pei, just as an operational check. If difference between Pei and Peo is too great, trigger a corrective action. This probably means that the outflow from the endoscope (or the inflow) is blocked, or there is a leak.
6. Calculate Fnet using:

$$Fnet=Fi-Fo.$$

Accumulate Fnet and if it exceeds a warning limit, trigger corrective action to deal with excess fluid accumulating in operating cavity, or a leak in system.

According to one embodiment, the control unit 19 is adapted to calculate an estimated pressure Pei in the body cavity 3 based on the measured deliver pressure Pi, a static pressure difference between the body cavity 3 and the pressure at the first fluid pressure measuring device 22 Ph, and a pressure drop Pdi in the fluid line 10 between the first fluid pressure measuring device 22 and the body cavity 3, wherein the control unit 19 is further adapted to compare the control signal which corresponds to an actual target for the deliver pressure DP-at, with the estimated pressure Pei and adjust the first fluid pump device 21 and/or the second fluid pump device 18 to bring Pi to a pressure such that Pei=DP-at.

According to one embodiment, the control unit 19 is adapted to calculate an estimated pressure Peo in the body cavity (3) based on the measured pressure of the fluid leaving the body cavity (3), the static pressure difference between the body cavity 3 and the pressure at the first fluid pressure measuring device 22 Ph and/or the second fluid pressure measuring device 23, and a pressure drop in the fluid line 16 between the body cavity 3 and the second fluid pressure measuring device 23, wherein the control unit 19 is further adapted to compare Peo with Pei and trigger a corrective action if the difference between Peo and Pei is greater than a threshold value, wherein the threshold value is e.g. >10%

According to one embodiment, a method is provided, comprising the steps:

measuring the deliver pressure Pi, corresponding to the pressure of the fluid delivered to the body cavity 3,
determining a pressure difference between the body cavity (3) and the pressure at a first fluid pressure measuring device 22 Ph,
determining a static pressure drop Pdi in the fluid line 10 between the first fluid pressure measuring device 22 Ph and the body cavity 3
calculating Pei=Pi−Ph−Pdi,
comparing Pei with the actual target for the deliver pressure (DP-at),
adjusting Pi such that Pei=(DP-at).

According to one embodiment, a method is provided, further comprising the steps:
measuring the pressure of the fluid leaving the body cavity 3 Po,
determining the static pressure difference between the body cavity 3 and the pressure at the first fluid pressure measuring device 22 and/or the second fluid pressure measuring device (23) Ph,
determining a pressure drop Pdo in the fluid line (16) between body cavity (3) and the second fluid pressure measuring device (23),
calculating Peo=Po−Ph+Pdo
comparing Peo with Pei
triggering a corrective action if the difference between Peo and Pei is greater than a threshold value, wherein the threshold value is e.g. >10%, According to one embodiment, the control unit 19 is adapted to derive a control signal based on a signal from the blood pressure measuring device 20, wherein the control signal is derived by processing the signal from the blood pressure measuring device 20 by using a correlation factor and/or an adjustment factor and/or a compensation value, stored in the device, wherein the correlation factor is dependent on the relationship between a blood pressure measurement signal, and a perfusion pressure of the body cavity 3, the adjustment factor corresponds to a preferred required over pressure above the perfusion pressure of the body cavity 3, the compensation value corresponds to the height level difference between the position for blood pressure measurement and the body cavity 3, wherein the first fluid pump device and/or the second fluid pump device is adapted to control the pressure in the body cavity 3 based on said control signal received from the control unit 19. According to one embodiment, processing the signal by using a correlation factor and/or an adjustment factor, and/or a compensation value, comprises or equals multiplying the signal with the correlation factor and/or the adjustment factor, and/or the compensation value respectively. According to one embodiment, processing the signal comprises or equals calculating a control signal based on the correlation factor and/or an adjustment factor, and/or a compensation value. According to one embodiment, processing the signal comprises or equals mapping or comparing the received signal with stored data for blood pressure measurement signal and a related perfusion pressure, and/or adjustment factor and/or compensation value, According to one embodiment, the relationship between a blood pressure measurement signal and a perfusion pressure of a body cavity is known before-hand thus enabling this relationship to e.g. be pre-stored in the device 1.

A preferred embodiment of a device for irrigation and insufflation for endoscopy with blood pressure dependent pressure control according to the invention has been described. However, the person skilled in the art realizes that this can be varied within the scope of the appended claims without departing from the inventive idea.
All the described alternative embodiments above or parts of an embodiment can be freely combined without departing from the inventive idea as long as the combination is not contradictory.

The invention claimed is:

1. A device for irrigation and/or insufflation during endoscopic surgery or endoscopic procedures in a body cavity, comprising
a first fluid pump device in fluid connection with the body cavity via a fluid line, wherein the first fluid pump device is adapted to deliver a fluid to the body cavity,
a second fluid pump device in fluid connection with the body cavity via a fluid line, wherein the second fluid pump device is adapted to move a fluid from the body cavity,
a control unit connected to the first fluid pump device and/or the second fluid pump device,
a blood pressure measuring device, connected to the control unit, wherein the blood pressure measuring device is adapted to measure a blood pressure, and deliver a blood pressure measurement signal,
wherein the control unit is adapted to derive a control signal based on the signal from the blood pressure measuring device, wherein the control unit is further adapted to send the control signal to the first fluid pump device and/or the second fluid pump device,
wherein the control signal is derived by processing the signal from the blood pressure measuring device by using a correlation factor stored in the device, wherein the correlation factor is dependent on the relationship between the blood pressure measurement signal and a perfusion pressure of the body cavity,
wherein the first fluid pump device and/or the second fluid pump device is adapted to control the pressure in the body cavity based on said control signal received from the control unit.

2. The device according to claim 1, wherein the control signal is derived by processing the signal from the blood pressure measuring device by using an adjustment factor stored in the device corresponding to a preferred required over- or underpressure versus the perfusion pressure of the body cavity.

3. The device according to claim 2, wherein the control signal is derived by processing the signal from the blood pressure measuring device by using a compensation value stored in the device corresponding to a height level difference between a position for blood measurement and the body cavity.

4. The device according to claim 1, wherein a first fluid pressure measuring device is arranged to measure a deliver pressure Pi, corresponding to a pressure of the fluid delivered to the body cavity.

5. The device according to claim 4, wherein the control unit is adapted to calculate an estimated pressure Pei in the body cavity based on the measured deliver pressure Pi, a static pressure difference between the body cavity and the pressure at the first fluid pressure measuring device Ph, and a pressure drop Pdi in the fluid line between the first fluid pressure measuring device and the body cavity, wherein the control unit is further adapted to compare the control signal which corresponds to an actual target for the deliver pressure DP-at, with the estimated pressure Pei and adjust the first fluid pump device and/or the second fluid pump device to bring Pi to a pressure such that Pei=DP-at.

6. The device according to claim 1, wherein a second fluid pressure measuring device is arranged to measure a pressure of the fluid leaving the body cavity, wherein the second fluid pressure measuring device is connected to the control unit, wherein the control unit is further adapted to receive a fluid pressure measurement signal from the second fluid pressure measuring device and adjust the control signal based on said fluid pressure measurement signal.

7. The device according to claim 5 or 6, wherein the control unit is adapted to calculate an estimated pressure Peo in the body cavity based on the measured pressure of the fluid leaving the body cavity Po, the static pressure difference between the body cavity and the pressure at the first fluid pressure measuring device Ph and/or the second fluid pressure measuring device, and a pressure drop Pdo in the fluid line between the body cavity and the second fluid pressure measuring device, wherein the control unit is further adapted to compare Peo with Pei and trigger a corrective action if the difference between Peo and Pei is greater than a threshold value, wherein the threshold value is >10%.

8. The device according to claim 6, wherein the second fluid pressure measuring device is adapted to measure the pressure of the fluid leaving the body cavity after a certain time period has passed since the second fluid pump device has been set in an non-operating mode whereby the second fluid pump device has stopped moving fluid from the body cavity.

9. The device according to claim 8, whereby the second fluid pressure measuring device is adapted to measure the pressure of the fluid leaving the body cavity in one measurement and/or in several measurements under a time period whereby the mean fluid pressure is calculated.

10. The device according to claim 1, wherein the blood pressure measuring device comprises any one of a non-invasive blood pressure meter, an invasive blood pressure meter signal, or a monitoring equipment associated to endoscopic surgery or procedures.

11. The device according to claim 1, wherein the blood pressure measuring device is integrated in the device or is a separate external module.

12. The device according to claim 1, wherein processing the signal from the blood pressure measuring device by using a correlation factor stored in the device comprises or is defined by multiplying the signal from the from the blood pressure measuring device with the correlation factor stored in the device.

13. A method for controlling an irrigation or insufflation fluid pressure in a body cavity of a patient, comprising the steps of:
setting a default target deliver pressure (DP-dt) for the irrigation or insufflation fluid,
measuring a blood pressure, of said patient,
dynamically calculating a true perfusion pressure (PP-t) based on the measured blood pressure by processing a signal from a blood pressure measuring device by using a correlation factor,
automatically adjusting the default target deliver pressure (DP-dt) based on the true perfusion pressure (PP-t) into an actual target for the deliver pressure (DP-at).

14. The method according to claim 13, whereby the default target deliver pressure (DP-dt) corresponds to a normal perfusion pressure (PP-n) in a specific body cavity plus an adjustment factor (A) of 5-15% depending on the specific body cavity to prevent bleeding in the specific body cavity.

15. The method according to claim 14, whereby automatically adjusting the default target deliver pressure (DP-dt) to the actual target for the deliver pressure (DP-at) comprises:
calculating (PP-t+A) and comparing with (DP-dt),
increasing or decreasing (DP-dt) into (DP-at) if (PP-t+A) deviates from (DP-dt).

16. The method according to claim 15, further comprising:
setting a second fluid pump device in a non-operating mode whereby a second fluid pump device stops moving fluid from a body cavity,
measuring the pressure of the fluid leaving the body cavity after a certain time period has passed since the second fluid pump device has been set in a non-operating mode,
comparing (DP-at) with pressure of the fluid leaving the body cavity,
adjusting (DP-at) if deviates from the pressure of the fluid leaving the body cavity.

17. The method according to claim 16, further comprising providing a warning signal if (DP-at) deviates significantly from the pressure of the fluid leaving the body cavity, whereby significantly comprises more than >10%.

18. The method according to claim 13, further comprising the step:
continuously delivering a fluid deliver pressure to the body cavity according to (DP-at).

19. The method according to claim 13, further comprising the steps:
measuring a delivery pressure Pi, corresponding to the pressure of the fluid delivered to the body cavity,
determining a static pressure difference between the body cavity and the pressure at a first fluid pressure measuring device Ph,
determining a pressure drop Pdi in the fluid line between the first fluid pressure measuring device Ph and the body cavity
calculating Pei=Pi−Ph−Pdi,
comparing Pei with the actual target for the deliver pressure (DP-at),
adjusting Pi such that Pei=(DP-at).

20. The method according to claim 19, further comprising the steps:
measuring a pressure of the fluid leaving the body cavity Po,
determining a static pressure difference between the body cavity and the pressure at the first fluid pressure measuring device and/or a second fluid pressure measuring device Ph,
determining a pressure drop Pdo in the fluid line between body cavity and the second fluid pressure measuring device,
calculating Peo=Po−Ph+Pdo,
comparing Peo with Pei,
triggering a corrective action if the difference between Peo and Pei is greater than a threshold value, wherein the threshold value is >10%.

21. The method according to claim 13, whereby the actual target for the deliver pressure (DP-at) is dynamically adjusted regularly, based on the measured blood pressure.

22. The method according to claim 21, whereby the actual target for the deliver pressure (DP-at) is dynamically adjusted regularly every 2-5 seconds based on the measured blood pressure.

23. The method according to claim 13, further comprising the step of pressurizing the irrigation or insufflation fluid using a first fluid pump device according to claim 1.

24. The method according to claim 13, wherein processing the signal from the blood pressure measuring device by using a correlation factor stored in the device comprises or is defined by multiplying the signal from the from the blood pressure measuring device with the correlation factor stored in the device.

* * * * *